United States Patent [19]
Bezwada et al.

[11] Patent Number: 5,470,340
[45] Date of Patent: Nov. 28, 1995

[54] COPOLYMERS OF (P-DIOXANONE/GLYCOLIDE AND/OR LACTIDE) AND P-DIOXANONE

[75] Inventors: Rao S. Bezwada, Whitehouse Station, N.J.; Shalaby W. Shalaby, Anderson, S.C.; Donald F. Koelmel, Glen Gardener, N.J.

[73] Assignee: Ethicon, Inc., Somerville, N.J.

[21] Appl. No.: 132,595

[22] Filed: Oct. 6, 1993

[51] Int. Cl.$^6$ .................. A61B 17/04; C08G 63/08
[52] U.S. Cl. .................. 606/231; 606/230; 528/354; 524/411; 524/415
[58] Field of Search .................. 606/230, 231; 528/354, 357; 525/415, 937, 411

[56] References Cited

U.S. PATENT DOCUMENTS

| | | | |
|---|---|---|---|
| 4,052,988 | 10/1977 | Doddi et al. | 606/230 |
| 4,643,191 | 2/1987 | Bezwad et al. | 606/230 |
| 4,653,497 | 3/1987 | Bezwada et al. | 606/230 |
| 4,791,929 | 12/1988 | Jarrett et al. | 128/335.5 |
| 5,047,048 | 9/1991 | Bezwada et al. | 606/231 |
| 5,100,433 | 3/1992 | Bezwada et al. | 606/230 |
| 5,252,701 | 10/1993 | Jarrett et al. | 528/354 |
| 5,312,437 | 5/1994 | Hermes et al. | 606/230 |
| 5,314,989 | 5/1994 | Kennedy et al. | 528/354 |
| 5,320,624 | 6/1994 | Kaplan et al. | 606/230 |

FOREIGN PATENT DOCUMENTS

| | | |
|---|---|---|
| 0460428A2 | 6/1991 | European Pat. Off. . |
| 0509508A2 | 4/1992 | European Pat. Off. . |

*Primary Examiner*—Gary Jackson
*Attorney, Agent, or Firm*—Hal Brent Woodrow

[57] ABSTRACT

A copolymer of p-dioxanone and a prepolymer of p-dioxanone and lactide and/or glycolide, and absorbable surgical devices such as sutures, surgical meshes, surgical staples, hemostatic clips, suture knot clips, and the like made therefrom.

17 Claims, No Drawings

COPOLYMERS OF (P-DIOXANONE/GLYCOLIDE AND/OR LACTIDE) AND P-DIOXANONE

FIELD OF THE INVENTION

This invention relates to copolymers derived from p-dioxanone, and especially to crystalline copolymers having mechanical and biological properties which are desirable for the preparation of absorbable surgical sutures and devices.

BACKGROUND OF THE INVENTION

U.S. Pat. No. 4,052,988 describes p-dioxanone homopolymers and the preparation of absorbable filaments exhibiting mechanical and biological properties suitable for use as surgical sutures. Unlike previous absorbable synthetic sutures, for example sutures derived from homopolymers or copolymers of lactide or glycolide, p-dioxanone sutures are particularly well suited for use as monofilament sutures. Monofilament sutures made with p-dioxanone have enhanced flexibility and pliability compared to conventional absorbable synthetics sutures. Conventional absorbable synthetic sutures generally have a braided or twisted construction in a multifilament form to reduce the "stiff" feel of the suture. Unfortunately, multifilament sutures are often disadvantageous because their rough surface can often tear tissue during surgical procedures.

As good as the sutures derived from p-dioxanone are, there is still room for improvement. U.S. Pat. No. 4,643,191 describes copolymers of p-dioxanone and lactide, and absorbable sutures prepared therefrom. The lactide component of the copolymer may offer enhanced physical properties, for example, increased straight or knot tensile strength and reduced modulus, without sacrificing any of the other outstanding properties of a p-dioxanone homopolymer.

U.S. Pat. No. 4,653,497 describes absorbable sutures prepared from copolymers of p-dioxanone and glycolide. The glycolide component of the copolymer significantly increases the rate of in vivo absorption and the in vivo breaking strength retention properties of the copolymer, properties which can be extremely advantageous for certain surgical procedures.

A recent European Patent Application, EPA 460,428 A2, also describes copolymers of caprolactone, glycolide and lactide. This application describes a block copolymer formed by a two-stage polymerization process. In the first stage of this process a prepolymer is formed with a high content of a caprolactone type monomer such as p-dioxanone, the remainder of the prepolymer being a fast reacting glycolide type monomer. In the second stage of the polymerization the prepolymer is reacted with an additional fast reacting glycolide type monomer to provide a segmented block copolymer.

In view of the attempts described in the art to modify or enhance the properties of p-dioxanone homopolymers, it would be desirable to formulate a polymer composition which can offer increased flexibility and a controlled breaking strength retention (BSR) profile.

SUMMARY OF THE INVENTION

In one aspect of this invention we have discovered a copolymer comprising p-dioxanone and a prepolymer of p-dioxanone and a monomer selected from the group consisting of lactide, glycolide and combinations thereof.

In another aspect of the invention we have discovered an absorbable surgical filament prepared by melt spinning the copolymer described above.

The copolymer of this invention can be readily melt spun using conventional techniques. The fibers prepared from these copolymers have the combination of mechanical and biological properties necessary for use as an absorbable monofilament surgical suture. By varying the ratio of lactide or glycolide to p-dioxanone in the prepolymer, or by varying the concentration of prepolymer in the copolymer, the compliance and the in vivo absorption profile can be modified significantly. Therefore, the properties of copolymers of this invention can be tailored for specific applications.

The copolymers are useful for the preparation of surgical filaments, especially absorbable, monofilament surgical sutures, although these copolymers may find use in the preparation of surgical devices. For example, the copolymers may be used as surgical meshes, surgical staples, hemostatic clips, suture knot clips, and the like. The copolymers of this invention may be fashioned into surgical devices by conventional melt processing techniques.

DETAILED DESCRIPTION OF THE INVENTION

The copolymers of the present invention are composed of p-dioxanone and a prepolymer of p-dioxanone and lactide and/or glycolide. The copolymers are generally prepared by first forming the prepolymer by polymerizing p-dioxanone with lactide and/or glycolide, then chain extending the prepolymer with additional p-dioxanone monomer in a second polymerization.

The amount of prepolymer used to prepare the copolymers can vary over a wide range, and will depend to a great extent on the breaking strength retention and absorption properties desired. Typically, an amount of prepolymer ranging from about 5 to about 80 percent by weight of the composition of the copolymer is acceptable (wherein the total weight percent of the copolymer is 100 percent). An amount less than 5 percent prepolymer generally will not modify the properties of the copolymer relative to a p-dioxanone homopolymer, and amounts greater than 80 percent may adversely affect mechanical properties relative to a p-dioxanone homopolymer. An amount of prepolymer ranging from about 5 to about 40 weight percent is preferred.

The ratio of lactide or glycolide to p-dioxanone used to prepare the prepolymer must be adjusted so that the resulting prepolymer has a melting point of less than 120° C. This is important to facilitate the successful copolymerization of the prepolymer with p-dioxanone, since the p-dioxanone polymerizations are generally conducted at less than 120° C. to avoid a high residual monomer content in the final copolymer. Prepolymers exhibiting the properties desired for copolymerization with p-dioxanone can generally be prepared at a mole ratio of lactide or glycolide to p-dioxanone from in the range of about 50:50 to about 5:95, but a ratio in the range of from 30:70 to 10:90 is preferred. Generally, if the amount of lactide or glycolide exceeds 50 mole percent of the prepolymer, then the prepolymer would have a melting temperature greater than the desired temperature for copolymerizing with p-dioxanone and/or the solubility of the prepolymer in p-dioxanone may be very low. A prepolymer prepared from greater than 95 mole percent p-dioxanone would typically provide a copolymer exhibiting properties similar to a p-dioxanone homopolymer.

The prepolymer of lactide or glycolide and p-dioxanone at varying ratios of lactide or glycolide to p-dioxanone can be prepared by conventional polymerization techniques well known in the art, for example, as described in U.S. Pat. No. 4,653,497. Once the prepolymer is prepared, the copolymer can be prepared by polymerizing the desired proportions of prepolymer and p-dioxanone in the presence of an organometallic catalyst at elevated temperatures. The organometallic catalyst is preferably a tin-based catalyst, e.g. stannous octoate, and is present in the monomer mixture at a mole ratio of monomer to catalyst preferably ranging from 15,000 to 40,000/1. The initiator is typically an alkanol, a glycol, a hydroxy acid, or an amine, and is present in the monomer mixture at a mole ratio of monomer to initiator ranging from 400 to 2000/1. The polymerization can be carried out at a temperature range from 100° to 160° C., preferably 10°–140° C., until the desired molecular weight and viscosity are achieved; generally no longer than 16 hours is required. Alternatively, the polymerization can be carried out in two or more successive temperature steps, for example, for 1–2 hours at 100°–140° C. and then for 2–5 days at about 80° C.

In preferred embodiments, the copolymers of this invention have a degree of crystallinity and an intrinsic viscosity which render the copolymers suitable for extrusion into fibers or films, or for injection molding into surgical devices such as staples. Advantageously, the crystallinity of the copolymers will be greater than about 10 percent as measured by x-ray diffraction, to enable the copolymer to maintain its structural integrity at the elevated temperatures that may be encountered during the shipping and storage of surgical devices. Preferably, the inherent viscosity of the crystalline copolymers will range from about 0.8 to about 3.0, more preferably from about 1.2 to about 2.0 dL/g in a 0.1 g/dL solution of hexafluoroisopropyl alcohol (HFIP) at 25° C. A copolymer with an inherent viscosity below about 0.8 dL/g generally lacks sufficient molecular weight to provide suitable mechanical properties for surgical devices, and an inherent viscosity above about 3.0 dL/g is generally too viscous for melt processing.

After the desired copolymer is prepared, filaments exhibiting the requisite properties for use as surgical sutures may be prepared using conventionally accepted methods well known in the art by first melt extruding the copolymer through a spinnerette to prepare fibers, drawing the fibers to create molecular orientation, and then annealing the oriented fibers to enhance its performance characteristics. See, for example, U.S. Pat. Nos. 4,643,191 and 4,653,497, and 5,007,923 which also describe in detail the testing procedures suitable for determining the mechanical and biological properties of the monofilaments described in the attached examples.

As the term compliance or flexibility are used herein it refers to the force required to bend a filament or braided suture. The flexibility of a polymer is related to the Young's Modulus of the polymer. A high Youngs Modulus generally implies that a polymer will have a lower flexibility for individual filaments. Accordingly, it is highly desirable for sutures which must be twisted and tied in knots to be very flexible while retaining suitable tensile strength. The present invention provides copolymers that have a reduced Young's Modulus and retain a significant amount of tensile strength.

As the term is used in the claimed invention, the in vitro breaking strength retention (BSR) is a measure of the ability of a fiber to retain its strength after incubation in a buffer solution maintained at 50° C. It is the ratio of the breaking strength of the fiber after a predetermined period to the breaking strength before incubation. Therefore, the in vitro BSR is modified when the fiber loses its breaking strength after incubation over a shorter or longer period of time relative to the time required for a fiber derived from a p-dioxanone homopolymer to lose its breaking strength. The procedures for determining the in vitro BSR have been well documented and are described in the U.S. Pat. No. 4,643,191.

Similarly, an in vivo BSR is a measure of the ability of a fiber to retain its initial strength after implantation in an animal, e.g. a rat. An in vivo BSR is the ratio of the breaking strength of an implanted fiber after a predetermined period to the breaking strength of the fiber before implantation. The procedures for determining the in vivo BSR have been well documented and are described in the patent cited above. Another common suture property which is important to determine is the in vivo absorption profile.

The in vivo absorption profile is a profile generated over time of the amount of degradation that occurs to a section of a suture after implantation in a suitable test animal, e.g. a rat. This degradation is measured by calculating the median percent of the original cross-sectional area of the suture section remaining after an intramuscular implantation for a predetermined number of days. The in vivo absorption profile is modified when the amount of degradation for any given number of days after implantation is greater or less than the amount of degradation after the same period of time for a suture section derived from a p-dioxanone homopolymer. The procedures for determining the in vivo absorption profile are described in numerous patents, for example, U.S. Pat. No. 4,653,497.

Although the in vitro or in vivo BSR and the rate of absorption in vivo can be modified significantly to tailor such properties for a specific operative procedure, it is desirable to make such changes without sacrificing mechanical properties. In preferred embodiments, the straight tensile strength of a monofilament prepared from the copolymers of this invention is greater than 40,000 psi, preferably greater than 50,000 psi, and the knot tensile strength is greater than 30,000 psi, preferably greater than 40,000 psi. Additionally, the Young's Modulus of such an annealed monofilament is less than 250,000 psi, preferably less than 150,000 psi, and the percent elongation is less than 150, preferably less than 100.

The following examples are intended to illustrate preferred embodiments and are in no way intended to limit the scope of the claimed invention. As used in Table II, PDO, PGA and PLA refer to polymers derived from p-dioxanone, glycolide and lactide, respectively.

Example 1

Copolymer of (PDO/Glycolide)/PDO At (45/30)/25 Weight Percent

A flame dried, 250 milliliter, round bottom two neck flask was charged with 60 g (0.5877 mole) of p-dioxanone, 40.0 g (0.3446 mole) of glycolide, 0.286 milliliters of 1-dodecanol, and 0.085 milliliters of stannous octoate (0.33 molar in toluene), and dried under vacuum for about 16 hours at room temperature. The flask was fitted with a flame dried mechanical stirrer. The reaction flask was purged with nitrogen three times before venting with nitrogen. The reaction mixture was heated to 160° C. and maintained at 160°–180° C. for 2 hours. The oil bath temperature was dropped to 110° C. and 33.3 g (0.3262) of p-dioxanone were added to the prepolymer. The bath temperature was maintained at 110° C. for 4 hours under nitrogen atmosphere. The copolymer was isolated, ground, and dried under vacuum (0.1 mm Hg) at 80° C. for about 48 hours to remove any unreacted monomer. A weight loss of 27.8% was observed. The copolyester had a melting range of 140°–150° C. as determined by hot stage microscopy and an inherent viscosity of 2.15 dL/g in hexafluoroisopropanol (HFIP) at 25° C.

Example 2

Copolymers of (PDO/Glycolide)/PDO At (40/10)/50 by Weight Percent

A flame dried, 250 milliliter, round bottom two neck flask was charged with 40 g (0.3918 mole) of p-dioxanone, 10.0 g (0.0862 mole) of glycolide, 0.20 milliliters of 1-dodecanol, and 0.098 milliliters of stannous octoate (0.33 molar in toluene), and dried under vacuum for about 16 hours at room temperature. The flask was fitted with a flame dried mechanical stirrer. The reaction flask was purged with nitrogen three times before venting with nitrogen. The reaction mixture was heated to 160° C. and maintained at 160° C. for 2 hours. The oil bath temperature was then dropped and maintained 4 hours at 110° C., then 16 hours at 85° C. To the prepolymer, additional 50.0 g (0.4898) of p-dioxanone were added, and the bath temperature was maintained 24 hours at 90° C. and 72 hours at 80° C. The copolymer was isolated, ground, and dried under vacuum (0.1 mm Hg) at 80° C. for about 36 hours to remove any unreacted monomer. A weight loss of 17.6% was observed. The copolyester had a melting range of 94°–104° C. as determined by hot stage microscopy and an inherent viscosity of 1.62 dL/g in hexafluoroisopropanol (HFIP) at 25° C.

Example 3

Copolymers of (PDO/Glycolide) PDO at (45/5) 50 By Weight Percent

A flame dried, 250 milliliter, round bottom two neck flask was charged with 45 g (0.4408 mole) of p-dioxanone, 5.0 g (0.0431 mole) of glycolide, 0.20 milliliters of 1-dodecanol, and 0.098 milliliters of stannous octoats (0.33 molar in toluene), and dried under vacuum for about 16 hours at room temperature. The flask was fitted with a flame dried mechanical stirrer. The reaction flask was purged with nitrogen three times before venting with nitrogen. The reaction mixture was heated to 160° C. and maintained at 160° C. for 2 hours. The oil bath temperature was then dropped and maintained 4 hours at 110° C., then 16 hours at 85° C. To the prepolymer, additional 50.0 g (0.4898) of p-dioxanone were added, and the bath temperature was maintained 24 hours at 90° C. and 72 hours at 80° C. The copolymer was isolated, ground, and dried under vacuum (0.1 mmHg) at 80° C. for about 36 hours to remove any unreacted monomer. A weight loss of 15.0% was observed. The copolyester had a melting range of 100°–104° C. as determined by hot stage microscopy and an inherent viscosity of 1.85 dL/g in hexafluoroisopropanol (HFIP) at 25° C.

Example 4

This example describes the physical properties of fiber prepared from the copolymers described in Examples 1–3.

In the preparation of fiber, especially surgical filaments, the copolymers are melt extruded through a spinnerette in a conventional manner to form one or more filaments, in accordance with the following general procedure:

Extrusion of the copolymers described herein was accomplished using an INSTRON Capillary Rheometer. The copolymers were packed in the preheated (80° to 90° C.) extrusion chamber and extruded through a 40 mil die (L/D=24.1) after a dwell time of 9 to 12 minutes at the extrusion temperature and a ram speed of 2 cm/min. While extrusion temperatures depend both on the polymer Tm and on the melt viscosity of the material at a given temperature, extrusion of the subject copolymers at temperatures of about 10° to 75° C. above the Tm is usually satisfactory. The extrusion temperatures of the example copolymers described herein ranged from 120° to 205° C.

The extrudate was typically taken up through an ice water quench bath at 24 feet/minute, although other bath temperatures and take-up speeds were occasionally used. A screw-type extruder or similar device can be substituted for the INSTRON Capillary Rheometer.

The extrudate filaments are subsequently drawn about 6X to 7X in a one or multistage drawing process in order to achieve molecular orientation and improve tensile properties. The manner of drawing is as follows:

The extrudate (diameter range, 16–20 mils) is passed through rollers at an input speed of four feet per minute and into a heated draw bath of glycerine. The temperatures of the draw bath can vary from about 25° to 90° C.; the examples described herein employ temperatures between 49° and 58° C. The draw ratio in this first stage of drawing can vary from 3X to about 7X; the examples described herein employ first stage draw ratios from 4X to 5.5X.

The partially drawn fibers are then placed over a second set of rollers into a glycerine bath (second stage) kept at temperature ranging from 50° to 95° C.; the examples described herein employ second stage, but a ratio range of from 1.2X to 1.6X was employed in the examples. The fiber is passed through a water-wash, taken up on a spool, and dried. A set of hot rollers can be substituted for a portion or all of the glycerine draw bath. The resulting oriented filaments have good straight and knot tensile strengths.

Dimensional stability and in vitro tensile strength retention of the oriented filaments may be enhanced by subjecting the filaments to an annealing treatment. This optional treatment consists of heating the drawn filaments to a temperature of from about 40° to 90° C., most preferably from about 60° to 80° C., while restraining the filaments to control shrinkage. This process may begin with the filaments initially under tension or with up to 20% shrinkage allowed prior to restraint. The filaments are held at the annealing temperature for few seconds to several days or longer depending on the temperature and processing conditions. In general, annealing at 60° to 80° C. for up to about 24 hours is satisfactory for the copolymers of the invention. Optimum annealing time and temperature for maximum fiber in vivo strength retention and dimensional stability is readily determined by simple experimentation for each fiber composition. The annealed samples described below were annealed at 60° C. for 12 hours while being held under tension to avoid shrinkage.

The filaments thus produced may be fabricated into sutures or ligatures, attached to surgical needles, packaged, and sterilized by known techniques.

The characteristic properties of the filaments of the invention are readily determined by conventional test procedures.

The tensile properties (i.e., straight and knot tensile strengths, Young's Modulus, and elongation) displayed herein were determined with an INSTRON tensile tester. The settings used to determine the straight tensile, knot tensile, break elongation, and Young's Modulus were the following, unless indicated:

TABLE I

|  | Gauge Length (cm) | Chart Speed (cm/min) | Crosshead Speed (cm/min) |
|---|---|---|---|
| Straight Tensile | 12 | 20 | 10 |
| Knot Tensile | 5 | 10 | 10 |
| Break Elongation | 12 | 20 | 10 |
| Young's Modulus | 12 | 20 | 10 |

The straight tensile strength is calculated by dividing the force to break by the initial cross-sectional area of the fiber. The elongation at break is read directly from the stress-strain curve of the sample allotting 4⅙% per centimeter of horizontal displacement.

Young's Modulus is calculated from the slope of the stress-strain curve of the sample in the linear elastic region as follows:

$$\text{Young's Modulus} = \frac{\tan\theta \times GL \times CS \times SL}{XH \times XS}$$

$\theta$ is the angle between the slope and the horizontal, XS is the initial cross-sectional area of the fiber, SL is scale load, XH is the crosshead speed, CS is the chart speed, and GL is the gauge length. The SL may be selected to provide a $\theta$ close to 45°.

The knot tensile strength of a fiber is determined in separate experiments. The test article is tied into a surgeons's knot with one turn of the filament around flexible tubing of ¼ inch inside diameter and 1/16 inch wall thickness. The surgeon's knot is a square knot in which the free end is first passed twice, instead of once, though the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

The tensile strength values and Young's modulus (Y.M.) are reported as KPSI, or PSI×10³.

TABLE II

| Copolymers Example No. | Example 1 | Example 2 | Example 3 |
|---|---|---|---|
| Initial (PDO/Glycolide)PDO Weight Ratio | (45/30)25 | (40/10)50 | (45/5)50 |
| Sn(Oct)/Monomer Ratio | 1/45K | 1/30K | 1/30K |
| I.V., dL/g | 2.15 | 1.62 | 1.85 |
| M.P. °C. | 140–150° C. | 94–104° C. | 100–104° C. |
| PROPERTIES OF ORIENTED FIBERS | | | |
| Straight Tensile, KPSI | 56 | 55 | 72 |
| Knot Tensile, KPSI | 52 | 33 | 44 |
| Elongation, % | 50% | 107% | 84% |
| Young's Modulus, KPSI | 39 | 75 | 116 |
| PROPERTIES OF ANNEALED FIBERS | | | |
| Straight Tensile, KPSI | 45 | 48 | 67 |
| Knot Tensile, KPSI | 40 | 36 | 47 |
| Elongation, % | 31% | 75% | 54% |
| Young's Modulus, KPSI | 39 | 148 | 229 |
| In Vitro BSR 4 days 50° C. | 2.4% | 30% | 68% |

Comparing the data presented above with published data on glycolide/PDO copolymers such as are described in U.S. Pat. No. 4,653,497 (see Table II, col. 6, lines 24 et seq.), it is apparent that the inventive copolymers are very different. The inventive copolymers have significantly reduced Young's Moduli and different in vitro BSR profiles compared to the previously disclosed copolymers of glycolide/PDO. These differences will result in a suture that is more compliant, therefore, easier to handle and faster absorbing in patients.

Example 5

Copolymers of (PDO/L(–) Lactide)/PDO at (8.8/6.7)/84.5 by weight percent

A flame dried, 500 milliliter, round bottom three neck flask was charged in a nitrogen glove box with 13.2 g (0.129 mole) of p-dioxanone, 10.0 g (0.069 mole) of L(–) Lactide, 0.20 milliliters of 1-dodecanol, and 0.030 milliliters of stannous octoate (0.33 molar in toluene), and subsequently dried under vacuum for about 16 hours at room temperature. The flask was fitted with a flame dried mechanical stirrer. The reaction flask was purged with nitrogen and evacuated three times before venting with nitrogen. The reaction mixture was heated under nitrogen to 150° C. and maintained at 150° C. for 6 hours. A sample of the prepolymer was tested for inherent viscosity and found to be 0.50 dL/g. After cooling to room temperature, in the nitrogen glove box, 126.9 g (1.243 mole) of PDO monomer and 0.101 milliliters of stannous octoate (0.33 molar in toluene) were charged to the reaction flask and placed under vacuum for about 16 hours at room temperature. The reaction mixture was heated to and maintained at 75° C. under nitrogen for 1 hour to achieve a single phase, then the temperature was raised to 110° C. and maintained at 110° C. for six hours. The resulting copolymer was isolated, ground, and dried under vacuum (0.1 mm Hg) at 80° C. for about 96 hours to remove any unreacted monomer. A weight loss of 19.5% was observed. The copolyester had a melting range of 101°–111° C. as determined by hot stage microscopy and an inherent viscosity of 1.96 dL/g in hexafluoroisopropanol (HFIP) at 25° C.

The copolymer was extruded at 170° C. using a shear rate of 212.6 sec.$^{-1}$. The resulting extrudate was drawn in two stages (5×@56° C.+1.4×@72° C.) employing total draw ratio of 7X. The oriented, annealed (80° C./6.5 hours/5% relaxation) and sterilized fiber properties of these monofilaments are summarized below:

TABLE III

| Fiber Properties | | |
|---|---|---|
| Initial (PDO/Lactide)PDO Weight Ratio (8.8/6.7)/84.5 | Oriented | Annealed/ EO Ster. |
| Diameter (mil) | 7.8 | 8.0 |
| Straight Tensile strength (psi) | 89,780 | 74,340 |
| Knot Strength (psi) | 45,620 | 51,600 |
| Elongation (%) | 58 | 39 |
| Young's Modulus (psi) | 89,780 | 169,400 |
| In vivo BSR, %* | | |
| 21 Days | | 65% |
| 28 Days | | 51% |
| 42 Days | | 15% |

*These monofilaments were absorbed intramuscularly in rats by 154 days.

Example 6

Copolymers of (PDO/L(−) Lactide)/PDO at (10.9/3.9)/85.2 by weight percent

A flame dried, 500 milliliters, round bottom three neck flask was charged in a nitrogen glove box with 16.1 g (0.158 mole) of p-dioxanone, 5.7 g (0.040 mole) of L(−) Lactide, 0.26 milliliters of 1-dodecanol, and 0.030 milliliters of stannous octoate (0.33 molar in toluene), and subsequently dried under vacuum for about 16 hours at room temperature. The flask was fitted with a flame dried mechanical stirrer. The reaction flask was purged with nitrogen and evacuated three times before venting with nitrogen. The reaction mixture was heated to 120° C. under nitrogen and maintained at 120° C. for 6 hours. A sample of the prepolymer was tested for inherent viscosity and found to be 0.45 dL/g. The remainder of the copolymer was then devolatilized at 90° C. under high vacuum for about 32 hours, and about 3.2 g of the unreacted monomer was removed. The I.V. after the devolatilization was found to be 0.53 dL/g. In a nitrogen glove box, 125.4 g (1.23 mole) of PDO monomer and 0.096 milliliters of stannous octoate (0.33 molar in toluene) were charged to the reaction flask and dried under vacuum for about 16 hours at room temperature. The reaction mixture was heated to and maintained at 75° C. under nitrogen for 1 hour to achieve a single phase, then the temperature was raised to 110° C. and maintained at 110° C. for 6 hours. The resulting copolymer was isolated, ground, and dried under vacuum (0.1 mm Hg) at 80° C. for about 80 hours to remove any unreacted monomer. A weight loss of 19.7% was observed. The copolyester had a melting range of 102°–106° C. by hot stage microscopy and an inherent viscosity of 2.03 dL/g in hexafluoroisopropanol (HFIP) at 25° C.

The copolymer was extruded at 165° C. using a shear rate of 212.6 sec.$^{-1}$. The resulting extrudate was drawn in two stages (5×@56° C.+1.4×@70° C.) employing total draw ratio of 7X. The oriented, annealed (80° C./6.5 hours/5% relaxation) fiber properties of these monofilaments are summarized below:

TABLE IV

| Fiber Properties | | |
|---|---|---|
| Initial (PDO/Lactide)PDO Weight Ratio (10.9/3.9)/85.2 | Oriented | Annealed |
| Diameter (mil) | 7.5 | 8.0 |
| Straight Tensile strength (psi) | 93,260 | 84,100 |
| Knot Strength (psi) | 49,340 | 51,860 |
| Elongation | 50% | 42% |
| Young's Modulus (psi) | 176,500 | 101,100 |

We claim:
1. A copolymer formed by reacting
   a) 5 to 80 weight percent of a prepolymer of p-dioxanone and a monomer selected from the group consisting of lactide, glycolide and combinations thereof, which has a melting point of less than 120° C.;
   b) with p-dioxanone to obtain a copolymer with an inherent viscosity in the range of from about 0.8 to about 3.0 dL/g in a 0.1 g/dL solution of hexafluoroisopropyl alcohol at 25° C.

2. The copolymer of claim 1 wherein the crystallinity of the copolymer is greater than about 10 percent as measured by x-ray diffraction.

3. The copolymer of claim 2 wherein the inherent viscosity of the copolymer is in the range of from about 1.2 to about 2.0 dL/g.

4. The copolymer of claim 1 wherein the amount of prepolymer is in the range of from about 5 to about 40 weight percent.

5. The copolymer of claim 4 wherein the mole ratio of lactide or glycolide monomer to p-dioxanone in the prepolymer is in the range of from about 50:50 to about 5:95.

6. An absorbable surgical filament prepared from a copolymer formed by reacting
   a) 5 to 80 weight percent of a prepolymer of p-dioxanone and a monomer selected from the group consisting of lactide, glycolide and combinations thereof, which has a melting point of less than 120° C.;
   b) with p-dioxanone to obtain a copolymer with an inherent viscosity in the range of from about 0.8 to about 3.0 dL/g in a 0.1 g/dL solution of hexafluoroisopropyl alcohol at 25° C.

7. The absorbable surgical filament of claim 6 wherein the amount of prepolymer ranges from about 5 to about 40 weight percent.

8. The absorbable surgical filament of claim 7 wherein the mole ratio of lactide and/or glycolide monomer to p-dioxanone in the prepolymer is in the range of from about 50:50 to about 5:95.

9. The absorbable surgical filament of claim 6 wherein the filament exhibits a straight tensile strength greater than 40,000 psi and a knot tensile strength greater than 30,000 psi.

10. The absorbable surgical filament of claim 9 wherein the filament exhibits a straight tensile strength greater than 50,000 psi and a knot tensile strength greater than 30,000 psi.

11. The absorbable surgical filament of claim 10 wherein the filament exhibits a Young's Modulus less than 250,000 psi.

12. The absorbable surgical filament of claim 10 wherein the filament exhibits an elongation less than 100 percent.

13. The absorbable surgical filament of claim 6 wherein the filament is in the form of an absorbable monofilament suture.

14. The absorbable surgical filament of claim 6 wherein the filament is in the form of an absorbable multifilament suture.

15. The absorbable monofilament suture of claim 13 wherein the absorbable monofilament suture is attached to at least one needle.

16. The absorbable multifilament suture of claim 14 wherein the absorbable multifilament suture is attached to at least one needle.

17. A surgical device prepared from a copolymer formed by reacting a) 5 to 80 weight percent of a prepolymer of p-dioxanone and a monomer selected from the group consisting of lactide, glycolide and combinations thereof, which has a melting point of less than 120° C.;

b) with p-dioxanone to obtain a copolymer with an inherent viscosity in the range of from about 0.8 to about 3.0 dL/g in a 0.1 g/dL solution of hexafluoroisopropyl alcohol at 25° C.

wherein the surgical device is selected from the group consisting of surgical meshes, surgical staples, hemostatic clips, and suture knot clips.

* * * * *